United States Patent [19]

Holtkamp, Sr.

[11] Patent Number: Plant 6,526

[45] Date of Patent: Jan. 10, 1989

[54] AFRICAN VIOLET PLANT NAMED SHENANDOAH

[75] Inventor: Reinhold Holtkamp, Sr., Isselburg, Fed. Rep. of Germany

[73] Assignee: Gessellschaftsvertrag uber die Erfindergemeinschaft "Optimara", Rees Haffen, Fed. Rep. of Germany

[21] Appl. No.: 55,928

[22] Filed: Jun. 1, 1987

[51] Int. Cl.[4] ..... A01H 5/00

[52] U.S. Cl. ..... Plt./69

[58] Field of Search ..... Plt./69

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

An African violet plant named Shenandoah, characterized by its semi-double, dark blue flowers with wavy edges; nice bouquet formed on strong upright flower stems; vigorous growth habit; round to oval, medium green, slightly serrated leaves; and long lasting, non-dropping flowering habit.

1 Drawing Sheet

The present invention comprises a new and distinct cultivar of African violet plant, botanically known as *Saintpaulia ionantha,* and hereinafter referred to by the cultivar name Shenandoah.

The new cultivar was referred to during the breeding and selection process by the designation H34/3, and is a product of a planned breeding program. The new cultivar was originated from a cross made by applicant in a controlled breeding program in Haffen, Federal Republic of Germany. The female, or seed parent was a cultivar designated d198/5 blue. The male, or pollen parent was a cultivar designated GG4 Pink.

Shenandoah was discovered and selected by me as a flowering plant within the progeny of the stated cross in a controlled environment in Haffen, Federal Republic of Germany. Asexual reproduction of the new cultivar by leaf cuttings, as performed by me at Haffen, Federal Republic of Germany, has demonstrated that the combination of characteristics as herein disclosed for the new cultivar are firmly fixed and retained through successive generations of asexual reproduction.

Shenandoah has not been observed under all possible environmental conditions. The phenotype may vary significantly with variations in environment such as temperature, light intensity and day length. The following observations, measurements and values describe the new cultivar as grown in 10 cm pots in Haffen, Federal Republic of Germany and Nashville, Tenn. under greenhouse conditions which closely approximate those generally used in commercial practice.

The following traits have been repeatedly observed and are determined to be basic characteristics of Shenandoah which in combination distinguish this African violet as a new and distinct cultivar:

1. Semi-double, dark blue flowers with wavy edges.
2. Forms a nice bouquet on strong upright flower stems.
3. Profuse flowering.
4. Each plant has 9–10 stems, each of which carries 8–10 and more generally violet-shaped but more round looking flowers.
5. Vigorous grower.
6. Plant saleable 10–11 weeks after potting.
7. Medium green, round to oval leaves, slightly serrated.
8. Long-lasting, non-dropping flowers.

9. Seed capsules push slightly through.
10. After maturity the flowers dry off and remain on the peduncle without becoming infected by botrytis.

The accompanying color photographic drawing shows a typical specimen plant of the new cultivar. The colors appearing in the photograph are as true as possible with color illustrations of this type.

In the following description, color references are made to The Royal Horticultural Society Colour Chart (RHS), except where general colors of ordinary significance are referred to. Color values were taken under natural light conditions at approximately 2:00 p.m. in Nashville, Tenn. Under cooler growing conditions and more intensive lighting, the blue color is more intense.

Botanical classification: *Saintpaulia ionantha,* Ramat., cv. Shenandoah.

Parentage:

*Male parent.*—GG4 Pink.

*Female parent.*—d198/5 blue.

Propagation: The new cultivar holds its distinguishing characteristics through successive propagations by leaf cuttings and by division of shoots.

Plant: From 8 to 11 cm tall when grown in pots, and 25–29 cm in diameter when fully grown. The growth rate is vigorous.

*Leaves.*—Shape: Round to oval, slightly serrated, slightly shiny, hairy. Diameter: 70–80 mm wide and 80–90 mm long. Texture: Velvety. Ribs and veins: Upperside well visible, underside very well pronounced, light green and shiny. Color (upper side): Green 139 between A and B. Color (under side): Yellow green 147D. Petioles: Light green, occasionally with purplish touch.

*Flowers.*—Buds: Ball-shaped, hairy, 7–8 mm before opening, purple. Sepals: Five (5) in number, purplish green. Calyx: Funnel-shaped. Aspect: Spear-shaped, hairy. Peduncle: Strong, upright, purplish brown.

*Individual flowers.*—Size: 35 to 40 mm in diameter. Shape: Semi-double with slightly wavy edges. Color (upper side): Violet blue 89 between B and C. Color (under side): Violet blue 91A. Borne: Each flower stem carries 8–10 and more flowers on strong, upright, peduncles that are free standing above the leaves. Corolla: Compact flower head. Flowering habit: Flowers 9–10 weeks after potting.

Reproductive organs.—Stamens: 2–3 in number. Anthers: 2–3, composed of 4–6 anther cells, seed capsule pushes slightly through. Filaments: 4–5 mm long, yellowish green on one side, dark purple on the other. Pollen Color: Yellow 7A. Styles: 6–7 mm, purplish blue, base of ovary light green.

*Roots.*—Well established, white, turning slightly brownish when older.

Disease resistance: Good.

General observations: Shenandoah is a very attractive, vigorous grower with medium green, round to oval leaves that are slightly serrated. Approximately 9–10 weeks after potting the plant has developed 9–10 strong upright flower stems, each of which carries 8–10 and more dark blue semi-double flowers with slightly wavy edges. The flower color contrasts nicely with the bright yellow anthers. The flowers consist of double violet-shaped flowers positioned over each other (giving each flower a total of 10 petals), making the blossom look round. Occasionally there are additional little petals. The flowers form a compact flower head that is free standing above the leaves. The flowers are long-lasting and non-dropping, and the seed capsule pushes slightly through.

I claim:

1. A new and distinct cultivar of African violet named Shenandoah, as described and illustrated, and particularly characterized by its semi-double, dark blue flowers with wavy edges; nice bouquet formed on strong upright flower stems; vigorous growth habit; round to oval, medium green, slightly serrated leaves; and long lasting, non-dropping flowering habit.

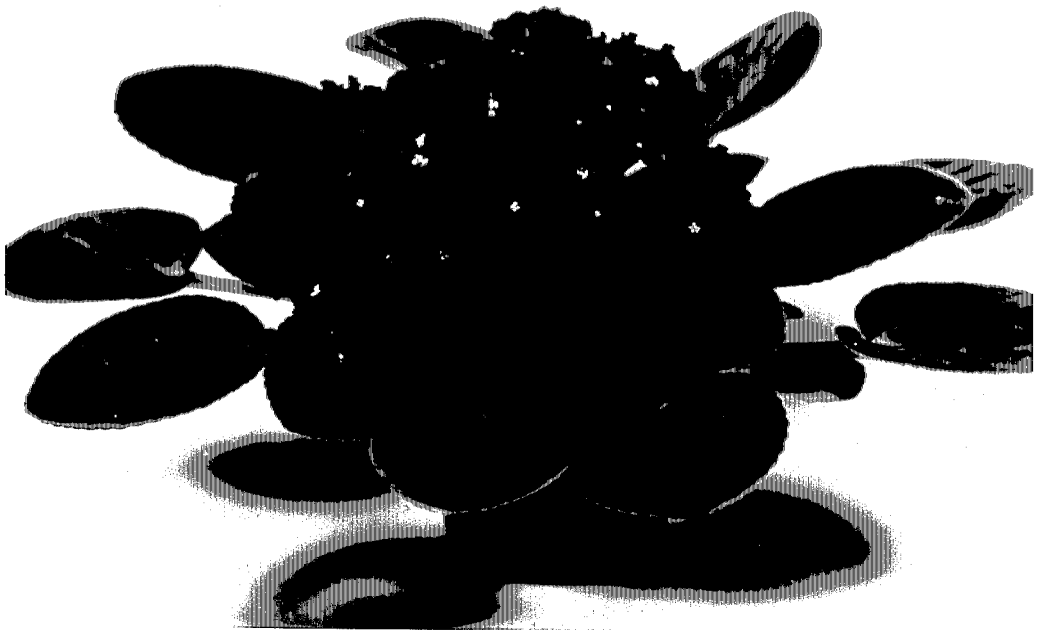

* * * * *